(12) United States Patent
Song et al.

(10) Patent No.: US 9,339,345 B2
(45) Date of Patent: May 17, 2016

(54) CUTTING APPARATUS FOR JOINT CUTTING SYSTEM USING ROBOT

(71) Applicant: CUREXO CO., LTD., Seoul (KR)

(72) Inventors: Chang Hun Song, Goyang-si (KR); YoungBae Park, Cheongju-si (KR); ChangHun Lee, Seoul (KR); DongHyun Son, Seoul (KR)

(73) Assignee: CUREXO, INC., Seoul (KR)

( * ) Notice: Subject to any disclaimer, the term of this patent is extended or adjusted under 35 U.S.C. 154(b) by 96 days.

(21) Appl. No.: 14/092,355

(22) Filed: Nov. 27, 2013

(65) Prior Publication Data

US 2014/0155911 A1    Jun. 5, 2014

(30) Foreign Application Priority Data

Nov. 30, 2012    (KR) .......................... 10-2012-0137674

(51) Int. Cl.
*A61B 17/32*    (2006.01)
*A61B 19/00*    (2006.01)
*A61B 17/16*    (2006.01)

(52) U.S. Cl.
CPC ......... *A61B 19/2203* (2013.01); *A61B 17/1633* (2013.01); *Y10S 901/41* (2013.01)

(58) Field of Classification Search
CPC ............... A61B 17/16; A61B 17/1628; A61B 17/1633; A61B 17/320016; A61B 17/32003; A61B 17/320758; A61B 2017/320028; A61B 2017/320032

See application file for complete search history.

(56) References Cited

U.S. PATENT DOCUMENTS

| | | | |
|---|---|---|---|
| 5,913,867 A * | 6/1999 | Dion | 606/180 |
| 2004/0122460 A1* | 6/2004 | Shores et al. | 606/180 |

FOREIGN PATENT DOCUMENTS

| | | |
|---|---|---|
| KR | 10-0873014 | 12/2008 |
| KR | 10-2012-0007030 | 1/2012 |

* cited by examiner

*Primary Examiner* — Melanie Tyson
(74) *Attorney, Agent, or Firm* — Kile Park Reed & Houtteman PLLC

(57) ABSTRACT

A cutting apparatus for joint cutting system using robot includes a shaft combined with a motor in a part of a robot arm, a cutter having a cutting head at the end of the shaft, a sleeve in which the shaft is inserted, and a cutter support member having a sleeve base where the sleeve is fixed, characterized in that the sleeve is a standalone member of a hollow bar with a center hole and is separable from and combinable with the sleeve base. The sleeve and the sleeve base are so separable that it is possible to reinforce the strength of the sleeve, which retrains the bending force to the sleeve, though the diameter of the sleeve is minimized.

10 Claims, 11 Drawing Sheets

PRIOR ART

PRIOR ART

PRIOR ART

CUTTING APPARATUS FOR JOINT CUTTING SYSTEM USING ROBOT

CROSS-REFERENCE TO RELATED APPLICATION

This application claims priority from Korean Patent Application No. 10-2012-0137674, filed on Nov. 30, 2012 in the Korean Intellectual Property Office, the disclosure of which is incorporated herein by reference.

BACKGROUND

1. Field

The present invention relates to a cutting apparatus for joint cutting system with robot. In detail, a sleeve and a sleeve base are so separable that it is possible to reinforce the strength of the sleeve, which retrains the bending force to the sleeve, though the diameter of the sleeve is minimized. Therefore, the durability of the sleeve is increased and the tough and damage to the bone, the muscle and the skin tissue around the surgical site are decreased owing to the decrease of the diameter of the sleeve. Also when the sleeve is bended the sleeve alone is so changeable that the maintenance cost is reduced and the maintainability is improved. In addition, the machinability of the bone is improved and it is so needless to change the cutter during the surgery that the surgery can be performed rapidly, exactly, and safely.

2. Description of the Related Art

The number of patient with joint disease comprising arthritis, osteoporotic fracture and etc. has been sharply increased as an aged population has been increased owing to the long average life span of human being.

The joint disease in early stage would be cured with non-surgery treatment comprising medication, physical therapy and so on, but the severe joint disease should be performed a surgery on.

Surgery treatment includes arthroscopic surgery, chondrocyte implantation and artificial joint surgery for the severe disease and etc.

The artificial joint surgery is performed in a way that the cutter of the cutting apparatus equipped in the end of variable-positioned arm of a robot rotates with cutting the knee joint according to the information from a computer, and then an artificial knee joint is put in (refer to FIG. 2).

FIG. 1 represents an existing cutting apparatus of joint cutting system with robot, and FIG. 2 represents roughly an artificial joint which is performed with on the knee joint. As depicted, a head 110 is 7.8 mm in a diameter and has a cutter on outer surface and front end surface formed at one end of the position-variable arm of the robot. A shaft 120 which is a hollow bar of 2.3 mm in a diameter is extended from head 110 and the back end of the shaft 120 is connected with a motor (M) equipped at the other end of the position-variable arm of the robot.

And outer circumferential surface of the shaft 120 is supported by a sleeve 130 fixed by the housing of the motor (M) such that the shaft 120 is rotatable. So the rotation of shaft 120 doesn't make any trembling and bending. The cutting is performed by the rotation of the head 110 which is protruded out from the sleeve 130.

The cutting apparatus of FIG. 1 has some drawbacks that the diameter of the head 110 is so large, as mentioned above, around 7.8 mm that it might touch skin tissue during an operation. And therefore the skin and the flesh are to be inevitably cut. Also a surgery to control the cutting path such like a tunnel cutting is not available. Also intense rolling friction between shaft 120 and sleeve 130 would abrade the surfaces after long-term using and make the unordinary rotations.

FIG. 3 shows other example of existing cutting apparatus of joint cutting system with robot which is disclosed in Korean registered patent No. 10-0873014.

Referring to FIG. 3, the joint cutting apparatus has a position-variable arm, a motor (M) at the front end of the arm, a sleeve 14 combined at housing of the motor, and a cutter 10 connected with a shaft of the motor to be rotatable in the sleeve. The cutter 10 comprises a shaft 11 of a hollow bar of cantilever type which is connected with the motor to be rotatable in the sleeve 14 and extended outward the sleeve, and a head 12 formed at the front end of the shaft 11. The cantilever length of the shaft 11 and the diameter of the head 12 are chosen as one of each 20-30 mm and 1.5-4.0 mm, or each 70-80 mm and 4.0-6.0 mm in order that the head 12 bores a hole into the bone.

As stated above, the cutting apparatus in FIG. 3 works with tunneling-like cutting method using cutter with minimal diameter and optimized cantilever length so that the bone would be cut safely and fast, and damage to the bone would be lessen, advantageously. But the shaft 11 is not supported by the sleeve 14 and has cantilever structure which cause disadvantageously trembling and bending. Especially, as the shaft 11 would be rotated over 60,000 rpm during an operation, there would be some drawbacks such like the breakdown of the shaft 11, unsafety and so on. Also, the trembling of the shaft 11 limits to the length of the protrusion in the cantilever structure so that it would be not available in deep surgical site.

Recently, in order to supplement the drawbacks of the cutting apparatus in FIG. 1 and FIG. 3, the diameter of the sleeve is decreased so that tough and damage to the bone, muscle, and skin tissue are lessened, and a cutter support member having multiple bearings in the sleeve has been developed.

However, the cutter support member of this type where the sleeve in the form a hollow bar and the sleeve base in the form of a cap are an integral unit has some defects such like difficult manufacturing, high manufacturing cost, long manufacturing. Especially, the integration of the sleeve and the sleeve base make it difficult to insert a tool into the inner hole of the sleeve or to form the settling groove of bearings on the inner surface of the sleeve so that the bearings should be inserted without the settling groove. Therefore, the diameter of the sleeve could not be decreased and the large diameter would make touch and damage to the bone, muscle, skin tissue around surgical site.

Besides, when the bearings inside the sleeve get damaged owing to the high speed rotation of the shaft of the cutter over 60,000 rpm or the sleeve gets bended by the bending force owing to the movement of the cutting head during the surgery, the sleeve base with the broken-down sleeve should be replaced with new integral unit so that the maintenance cost would be very high, disadvantageously.

Meanwhile, in the said existing cutting apparatuses one of the cutting heads of 7.8 mm and 2.3 mm in diameter is optionally used depending on the process and the cutting head should be changed properly during the surgery which is inconvenient to the operator and increases the surgery time. In other words, the cutting head of 7.8 mm in diameter is used in cutting the surface of the knee joint bone (ex, femur, tibia) on which the artificial joint is settled, and the cutting head of 2.3 mm in diameter is used in drilling the inserting hole (peg, hole in the knee joint bone), in which a fixing protrusion (a2) of the artificial joint (a) is inserted, after inconveniently changing the cutting head of 7.8 mm in diameter.

SUMMARY

An object of the present invention is to provide a cutting apparatus of a joint cutting system using robot, the diameter of the sleeve of which is decreased so as to reduce the touch and damage to the skin tissue.

Another object of the present invention is to provide a cutting apparatus of a joint cutting system using robot, the low maintenance cost and the improved maintainability of which are achieved by changing not the sleeve base but the bended sleeve alone.

Another object of the present invention is to provide a cutting apparatus of a joint cutting system using robot, with which the safe and rapid surgery is achieved by artificial joint surgery without changing the cutter and improved machinability.

The above objects are achieved by a cutting apparatus for joint cutting system using robot according to an aspect of the present invention, comprising; a shaft combined with a motor in a part of a robot arm, a cutter having a cutting head at the end of the shaft, a sleeve in which the shaft is inserted, and a cutter support member having a sleeve base where the sleeve is fixed, characterized in that the sleeve is a standalone member of a hollow bar with a center hole and is separable from and combinable with the sleeve base.

The sleeve might have support bearings which are equipped in the center hole and support the shaft 11 such that the shaft 11 is rotatable, and in order to reinforce the strength against the bending force the support bearings are located in the front side and the back side of the sleeve, which minimizes the reduction of the thickness of the sleeve. And the sleeve base might comprise a base body with middle hole part, first base join part formed on the inner circular surface around the front end of the sleeve base and combined with the back end of the sleeve, second base join part formed on the inner circular surface around the back end of the sleeve base and combined with the part of the robot arm, and a washing water discharging hole formed in the base body for discharging washing water, and the sleeve might comprises a sleeve body of a hollow bar shape, a join body with sleeve join part combined with the first base join part at the back end of the sleeve body, bearing install grooves located apart each other on the inner circular surface of the sleeve body for equipping the support bearings, reinforcing part for reinforcing against the bending force to the sleeve body which is protruded toward center of the center hole from the inner circular surface between the bearing install grooves.

Also the bearing install grooves might consist of first bearing install groove formed on the inner circular surface of the join body with the sleeve join part and second bearing install groove formed on the inner circular surface around the front side of the sleeve body, and the support bearings might consist of first support bearing combined at the front side of the first bearing install groove, second support bearing combined at the back side of the second bearing install groove, third support bearing combined at the back side of the first bearing install groove, and the fourth support bearing combined at the second bearing install groove.

Furthermore, each of the first to fourth support bearings might have multiple bearings consecutively arranged, the outside surface of which comes into contact with the first or second bearing install groove and the inside surface of which comes into contact with the outer circular surface of the shaft. And the above cutting apparatus might further comprise reinforcing spacers which are equipped on the inner circular surface of the sleeve between the second and fourth support bearings and between the first and third support bearings and which has a center hole where the shaft is inserted.

Meanwhile, the cutting apparatus might further comprise end spacers for retraining the fluctuation of the shaft which are inserted in the front and back ends of the center hole of the sleeve and have a center hole where the shaft is inserted.

Preferably, the cutting head has multiple cutters protruded equi-angularly at a head core, and the outer diameter of the cutting head corresponds to the diameter of a fixing protrusion of the knee joint implant or is bigger than the diameter of the fixing protrusion by within 10%.

Preferably, the number of the cutters is 5 and the outer diameter of the cutting head is 6.2 mm within a tolerance of 10% or the cutters have roughing groove for improving machinability.

The cutting apparatus for the joint cutting system according to the present invention has the following advantages:

The sleeve and the sleeve base are so separable that it is possible to reinforce the strength of the sleeve, which retrains the bending force to the sleeve, though the diameter of the sleeve is minimized. Therefore, the durability of the sleeve is increased and the tough and damage to the bone, the muscle and the skin tissue around the surgical site are decreased owing to the decrease of the diameter of the sleeve so that the safeness of the surgery is improved and patient's recovery time is shortened. And, after overlong use not a unit of the sleeve and the sleeve base, such like existing all in one type, but the sleeve alone is so changeable that the advantage is achieved that the maintainability is improved and the maintenance cost is decreased.

Also, trembling of the cutter is minimized, the machinability of the cutting head is improved, the surgery time is shortened, it is needless to change the cutter because with just one cutter it is possible to cut not only femur, tibia but also inserting hole (peg) where the fixing protrusion of the implant is inserted and therefore the surgery can be performed rapidly, exactly, and safely.

DETAILED DESCRIPTION OF EXEMPLARY EMBODIMENTS

Hereinafter, an embodiment of the present invention would be explained referring to appended drawings.

Figure 4:
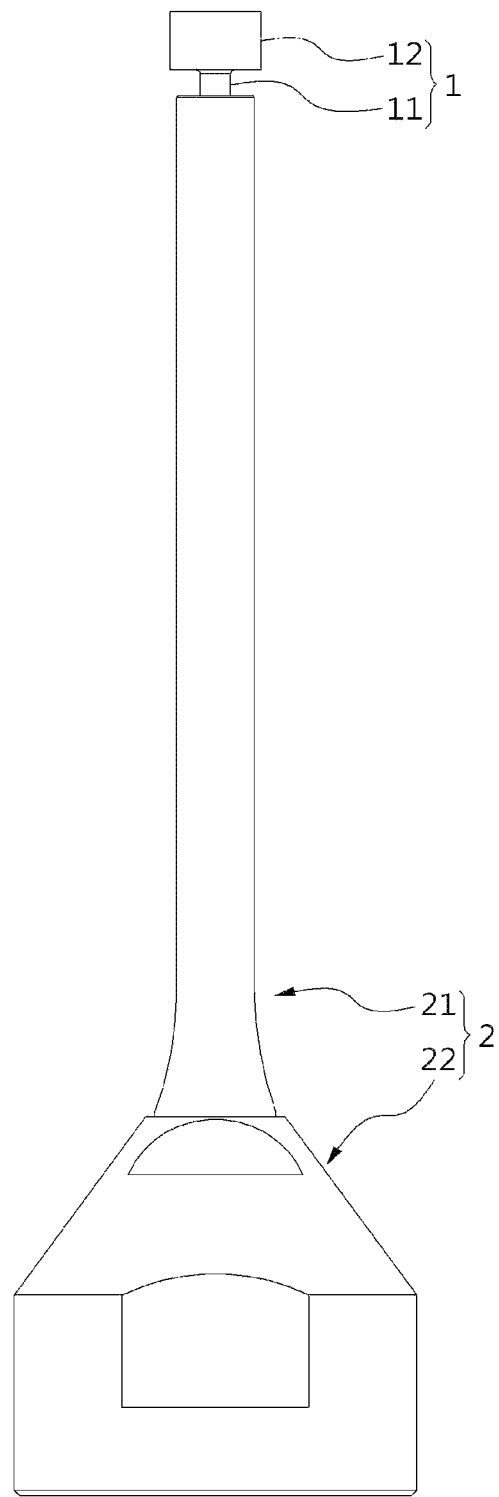
FIG. 4 is a front view of a cutting apparatus of a joint cutting system using robot according to an embodiment of the present invention.
Figure 5A:
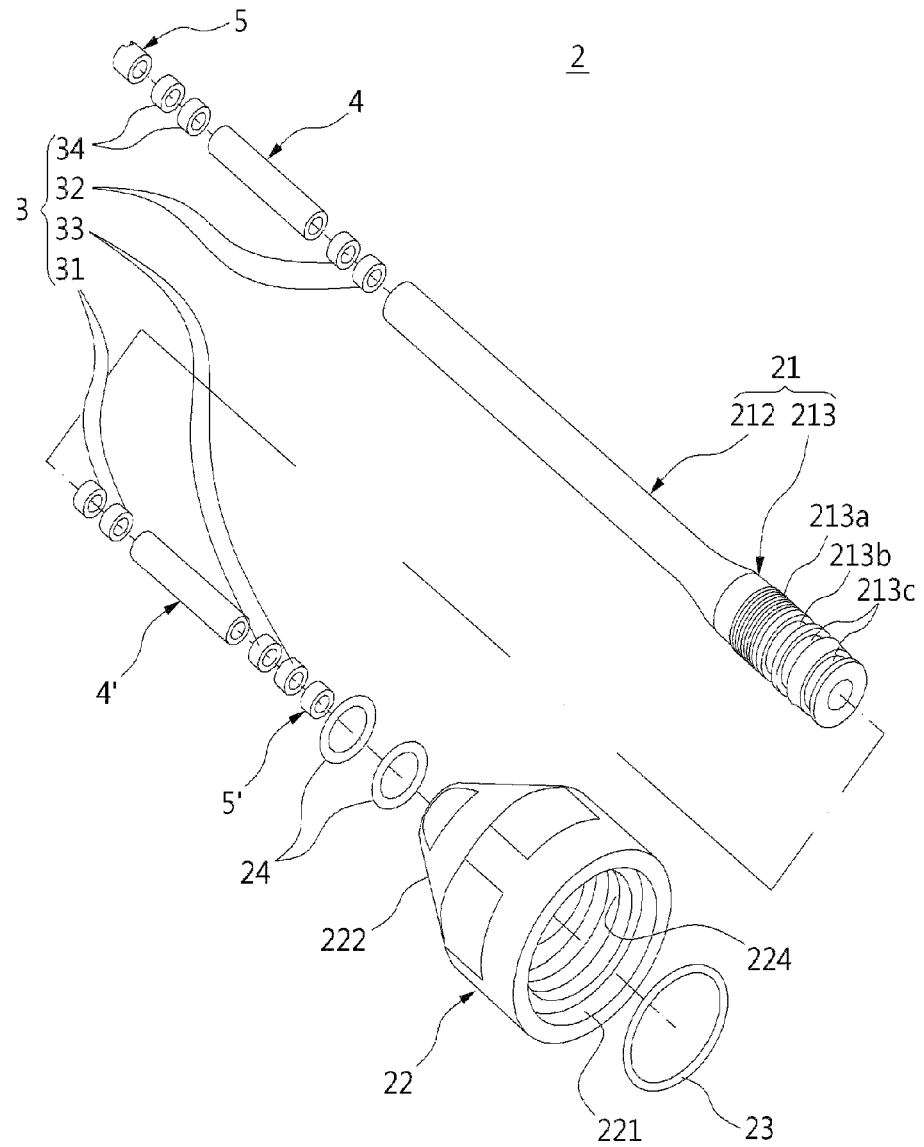
FIG. 5a is a perspective view of a cutting apparatus of a joint cutting system using robot according to an embodiment of the present invention.
Figure 5B:
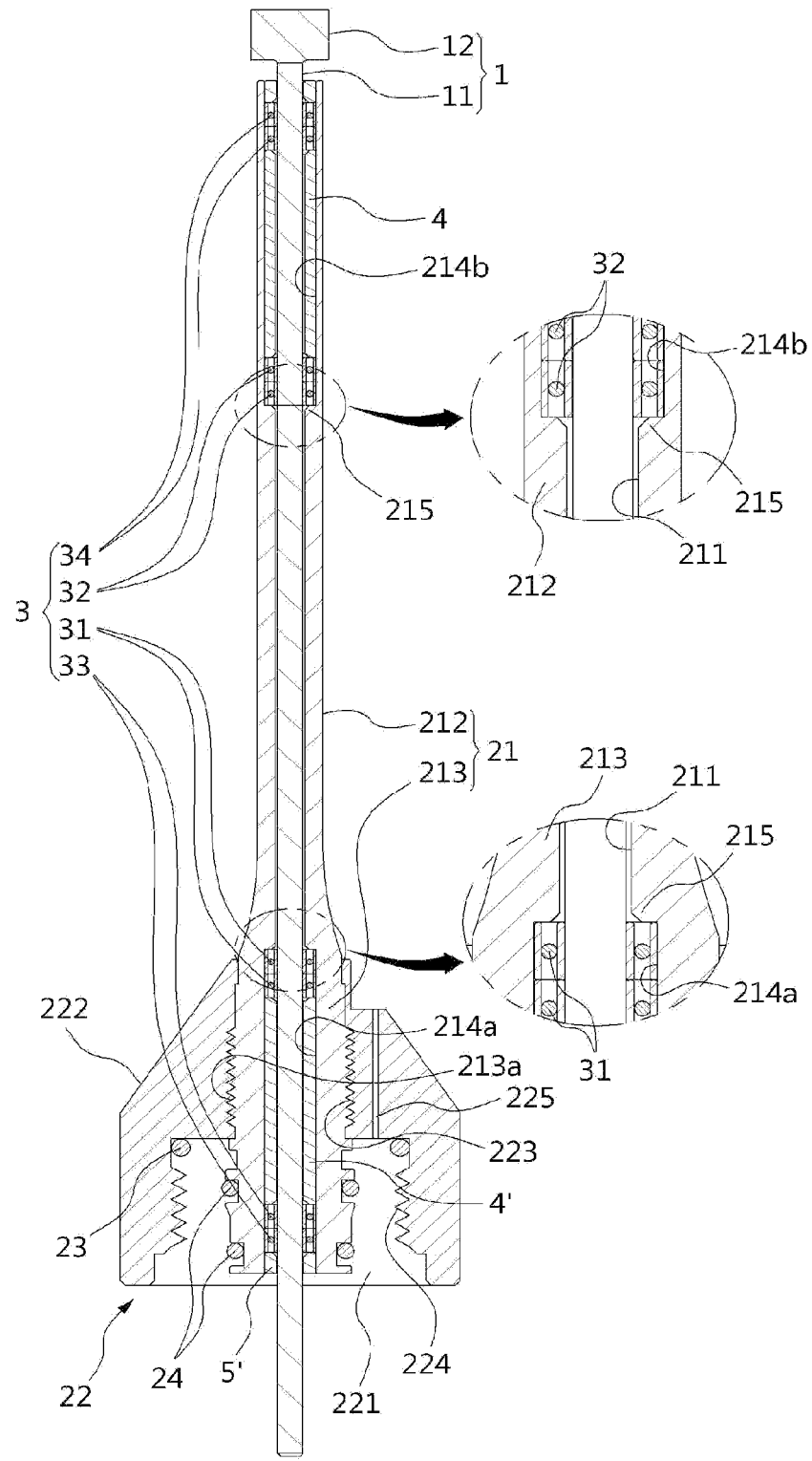
FIG. 5b is a sectional view of a cutting apparatus of a joint cutting system using robot according to an embodiment of the present invention.

FIG. 4 is a front view of a cutting apparatus of a joint cutting system using robot according to an embodiment of the present invention, FIG. 5a is a perspective view of a cutting apparatus of a joint cutting system using robot according to an embodiment of the present invention, and FIG. 5b is a sectional view of a cutting apparatus of a joint cutting system using robot according to an embodiment of the present invention.

Referring to FIG. 4 to FIG. 5b, a cutting apparatus of a joint cutting system according to an embodiment of the present invention is an apparatus installed at the arm (not shown) of a surgical robot which cuts bone to implant artificial joint such like a knee joint, and comprises a cutter 1 and a cutter support member 2, wherein the cutter 1 has shaft 11 connected with a motor (not shown) of the robot arm and a cutting head 12 formed at the end of the shaft 11, and the cutter support member 2 has a sleeve 21 where the shaft 11 is inserted and a sleeve base 22 which the sleeve 21 is fixed on.

Especially, in the cutting apparatus of the joint cutting system using robot according to the present invention, the sleeve 2 and the sleeve base 22 of the cutter support member 2 are so separable that the sleeve 21 is a standalone member of a hollow bar having a center hole 211 inside and is optionally combined with or separated from the sleeve base 22.

And, support bearings 3 are equipped inside the center hole 211 of the sleeve 21 for supporting the shaft 11 to be rotatable. The point is that considering the strength against the bending force, the support bearings 3 are located at the front side and back side of the sleeve 21 in order to minimize the decrease of thickness of the sleeve 21.

Figure 6:
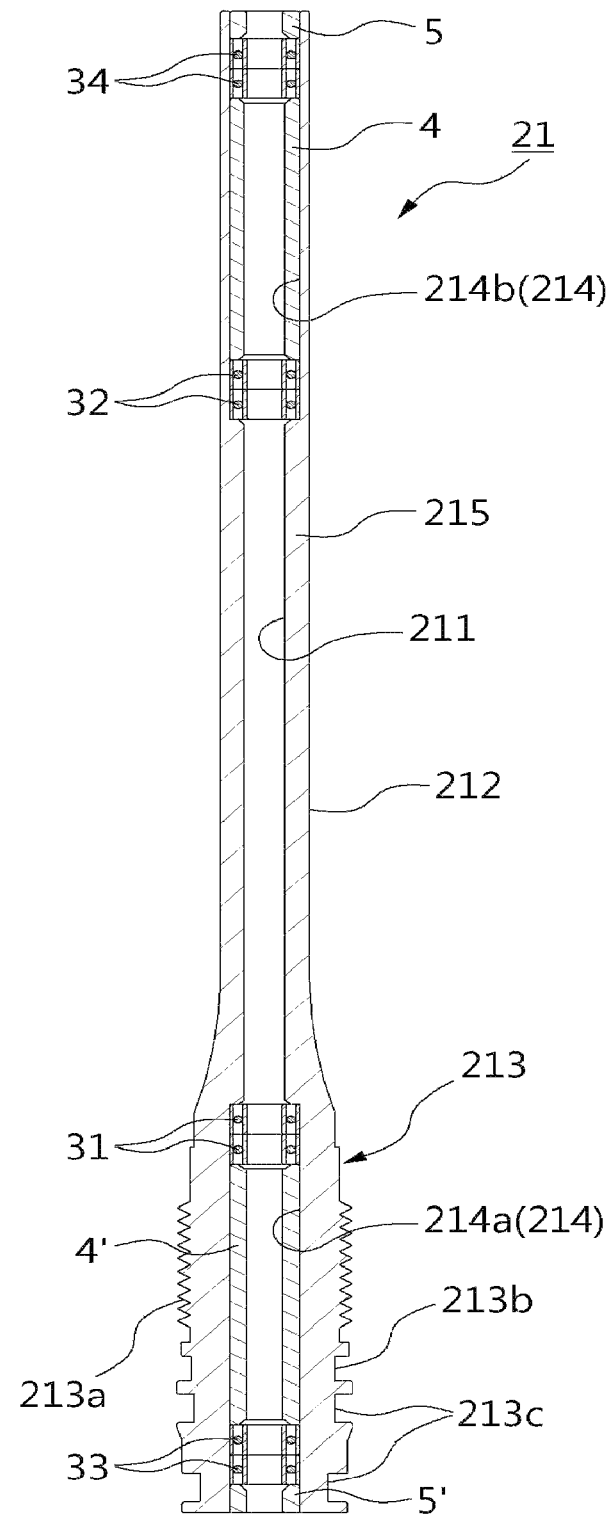
FIG. 6 is a sectional view of a sleeve adapted to a cutting apparatus of a joint cutting system using robot according to an embodiment of the present invention.

FIG. 6 is a sectional view of a sleeve adapted to a cutting apparatus of a joint cutting system using robot according to an embodiment of the present invention.

Referring to FIG. 6, the sleeve 21 is a member of a hollow bar type with a center hole 211 and comprises a sleeve body 212, a join body 213, bearing install groove 214, and reinforcing part 215.

The sleeve body 212 is a part inserted into the human body in surgery and is made a hollow bar member with uniform outer diameter. The length of the sleeve body 212 depends on the surgical site, the way of surgical operation and etc., and the length of the sleeve body 212 for knee joint surgery is preferably around 77 mm with 10% tolerance for error. Any material which is not harmful to the human body is adaptable for the sleeve body 212 and in this embodiment stainless of standard SUS303 is used.

The join body 213 is a part extended from the back end of the sleeve body 212 and forms one body with the sleeve body 212. It has sleeve join part 213a which is combined with latter mentioned first base join part 223 of the sleeve base 22, sealing insert groove 213b in which a sealing 23 is inserted, and o-ring insert groove 213c in which an O-ring 24 is inserted.

The bearing install groove 214 is formed on the inner circular surface of the sleeve 21 for installing the support bearing 3 and a couple of the bearing install grooves is located around front side and back side of the sleeve 21 apart each other.

Also, the bearing install groove 214 consists of first bearing install groove 214a on the inner circular surface of the sleeve 21 near the join body 213 and second bearing install groove 214b on the inner circular surface around the front side of the sleeve body 212

The reinforcing part 215 is formed in a state to protrude inward center hole 211 between the first bearing install groove 214a and the second bearing install groove 214b and to make the sleeve body 212 thicker for reinforcing the sleeve body 212 against bending force.

Meanwhile, the support bearing 3 comprises first support bearing 31 installed around the front end (bordering the reinforcing part 215) of the first bearing install groove 214a, second support bearing 32 installed around the back end (bordering the reinforcing part 215) of the second bearing install groove 214b, third support bearing 33 installed around the back end of the first bearing install groove 214a, and fourth support bearing 34 installed around the front end of the second bearing install groove 214b, Each of the first to fourth support bearing 31, 32, 33, 34 has consecutively arranged multiple bearings, which are installed to be inserted between the shaft 11 and the bearing install groove 214. Good-durability bearing which is capable of supporting the high speed rotation of the shaft 11 is not limited for the first to fourth support bearing 31, 32, 33, 34, and, however, in this embodiment two ball bearings are consecutively arranged in the first to fourth support bear 31, 32, 33, 34.

Also, reinforcing spacers 4, 4' are inserted between the support bearings to prevent bending of the sleeve body 212. The reinforcing spacer 4 is between the second and fourth support bearing 32, 34 on the inner circular surface of the sleeve 21 and the reinforcing spacer 4' is also between the first and third support bearing 31, 33, wherein the length of the reinforcing spacer 4, 4' corresponds to the separation distance of the support bearings. The reinforcing spacers 4, 4' have formed to have a center hole where the shaft 11 is inserted. Therefore, the reinforcing spacers 4, 4' fix the location of the support bearing 3 so as to prevent the support bearing 3 loose, and restrain the trembling of the shaft 11 around the section with no bearing.

Meanwhile, the sleeve 21 comprises end spacers 5, 5' for restraining the fluctuation of the shaft 11 in rotation. The end spacers 5, 5' are inserted in the ends of the center hole 211 and are much shorter than the reinforcing spacers 4, 4'. The end spacer 5 is in the center hole 211 at the front end of the sleeve body 212 and the end spacer 5' is in the center hole 211 at the back end of the sleeve body 212, wherein the end spacers 5, 5' are put in and fixed with forced insertion, welding or adhesive for metal (loctite 609).

The end spacer 5 withstands the force from the rotation and movement of the shaft 11 to the front end of the sleeve 21 and, as a result, the bending and trembling of the shaft 11 can be restrained.

Figure 7A:
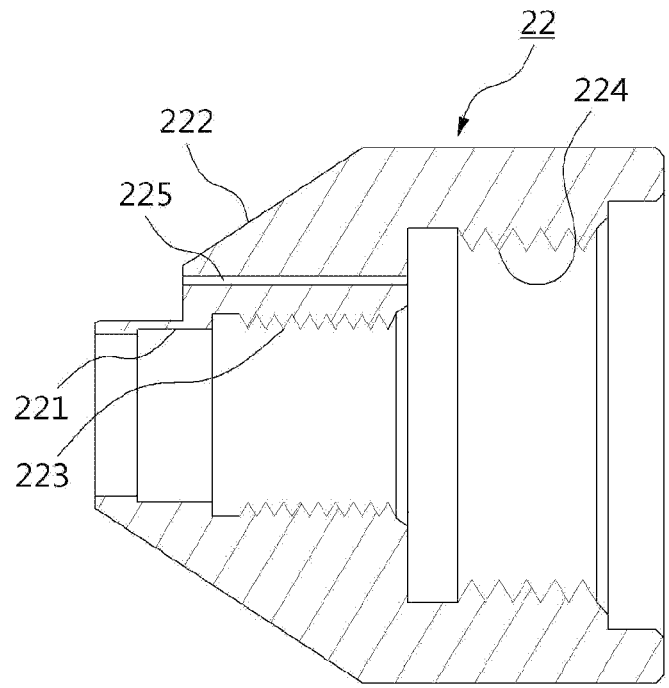
FIGS. 7a to 7c are views of a sleeve base adapted to a cutting apparatus of a joint cutting system using robot according to an embodiment of the present invention.
Figure 7B:
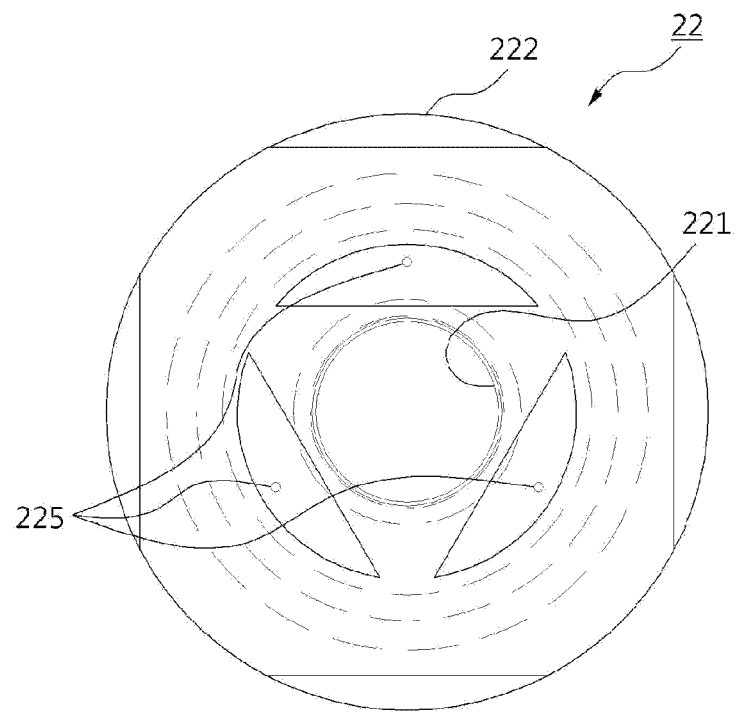
Figure 7C:
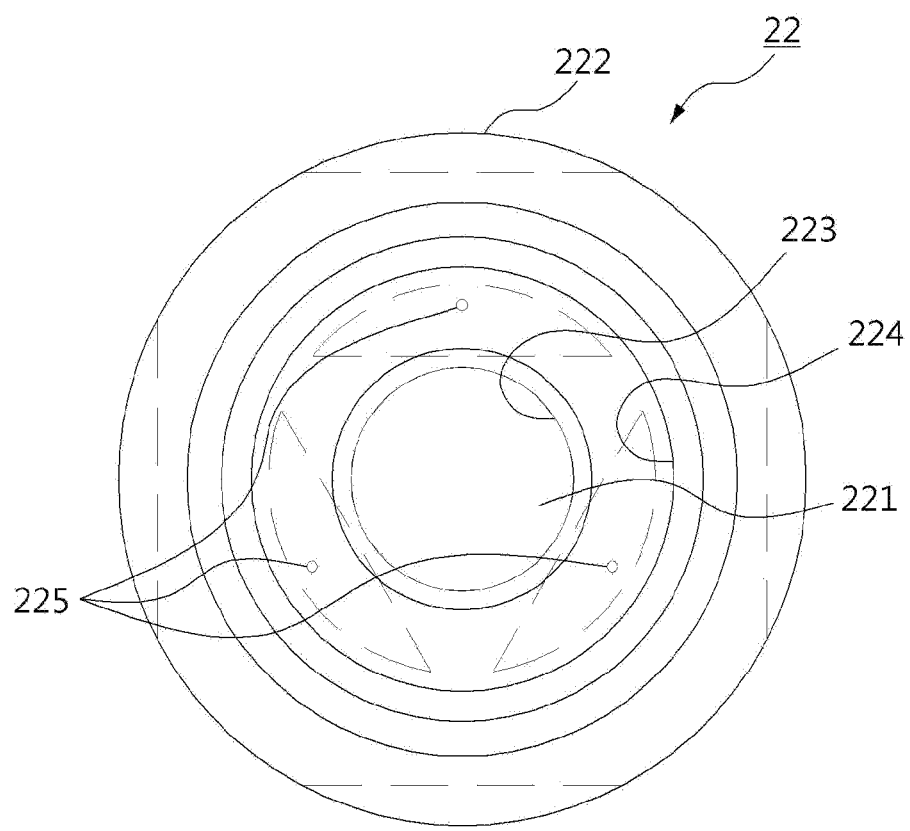

FIGS. 7a to 7c are each sectional view, left side view, and the right side view of a sleeve base adapted to a cutting apparatus of a joint cutting system using robot according to an embodiment of the present invention.

Referring to FIGS. 7a to 7c, the sleeve base 22 has a base body 222 in which first base join part 223, second base join part 224, and washing water discharging hole 225 are formed.

The base body 222 has a shape of a conic cap with middle hole part 221 in the center, and the middle hole part 221 comprises a hole part with large inner diameter to insert the join part of the robot arm into and another hole part with relatively small inner diameter to insert the join body 212 of the sleeve 21 into.

The first base join part 223 is the form of a female thread on the inner circular surface of the front side of the base body 222, which is combined with the sleeve join part 213a at the back side of the sleeve 21.

The second base join part 224 is the form of a female thread on the inner circular surface of the back side of the base body 222, which is combined with the join part (not shown) of the robot arm.

The washing water discharging hole 225 is formed of a hole like a tunnel passing forward from the middle hole part 221 through the base body 222 for discharging washing water during artificial joint surgery. The washing water discharging hole 225 has multiple holes and in this embodiment 3 holes are distributed at equiangular positions. And besides the function of the washing, the washing water discharged through the washing water discharging hole 225 performs the function of cooling for preventing the cutting friction heat doing damages to the cut site of the bone FIG. 8a is a perspective view of an exemplary cutter adapted to a cutting apparatus of a joint cutting system using robot according to an embodiment of the present invention.

Figure 1:
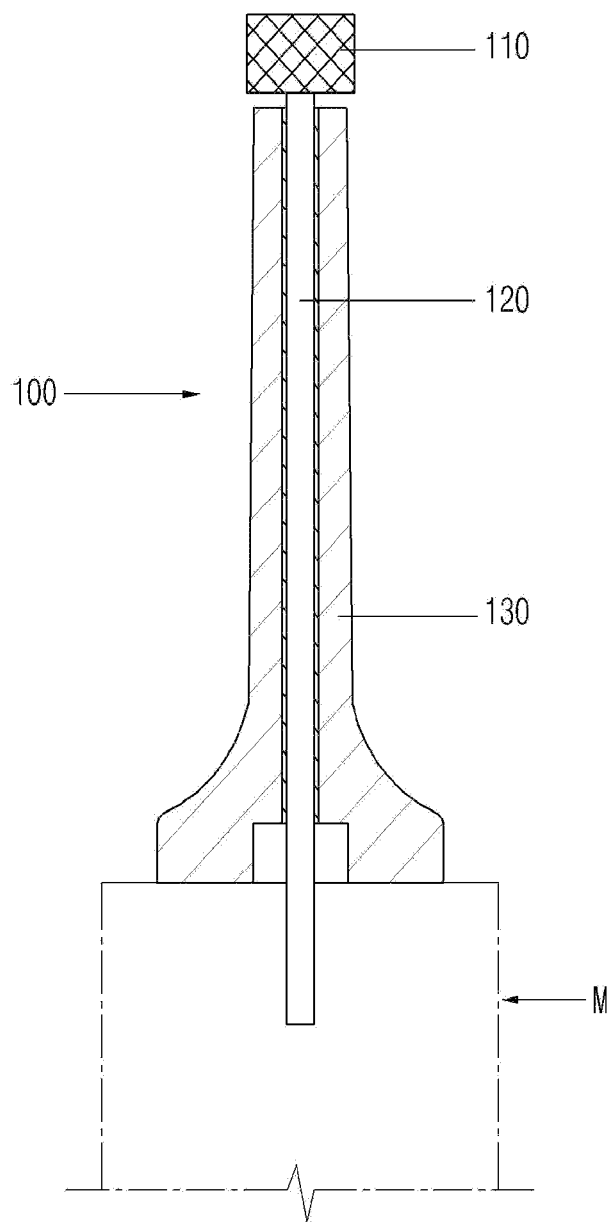
FIG. 1 is a schematic view of a cutting apparatus of an existing joint cutting system using robot.
Figure 2:
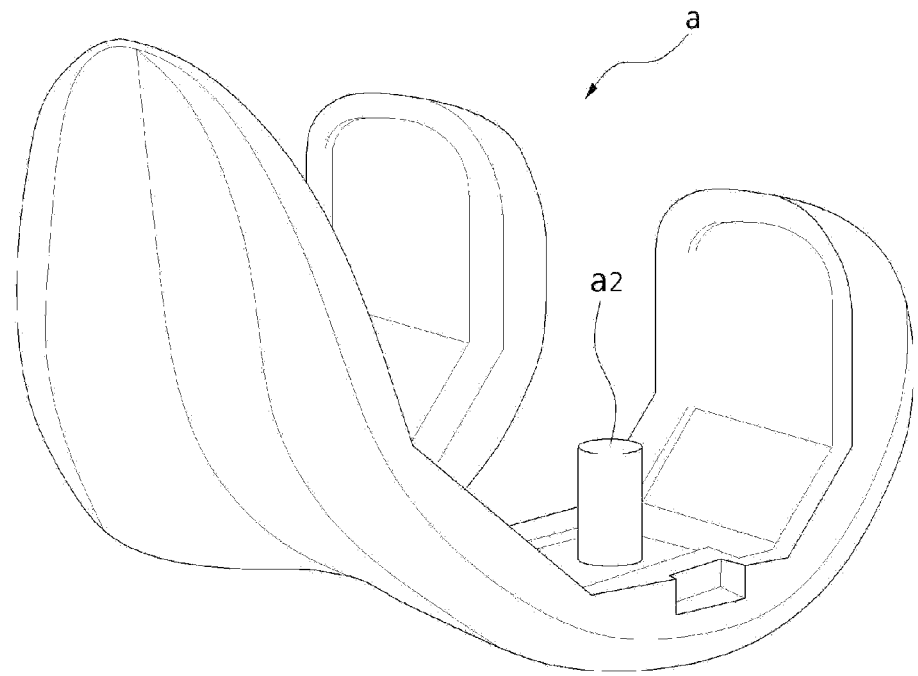
FIG. 2 is a perspective view of an exemplary artificial joint placed surgically on knee joint.
Figure 3:
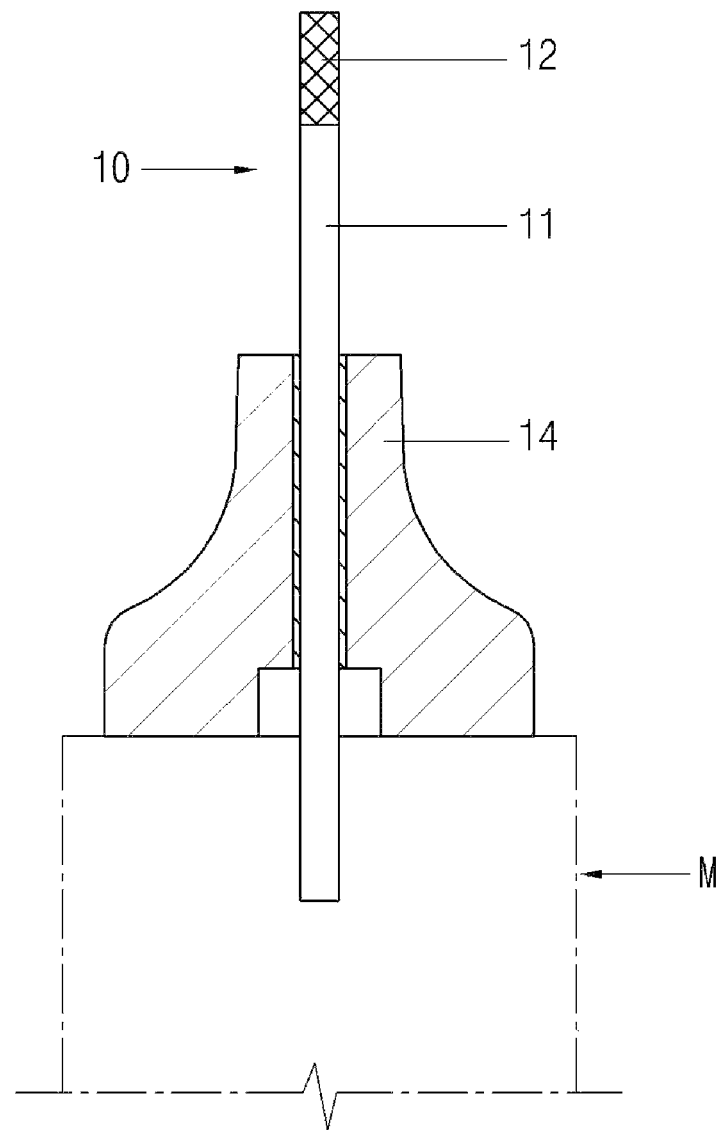
FIG. 3 is a schematic view of a cutting apparatus of another existing joint cutting system using robot.
Figure 8A:
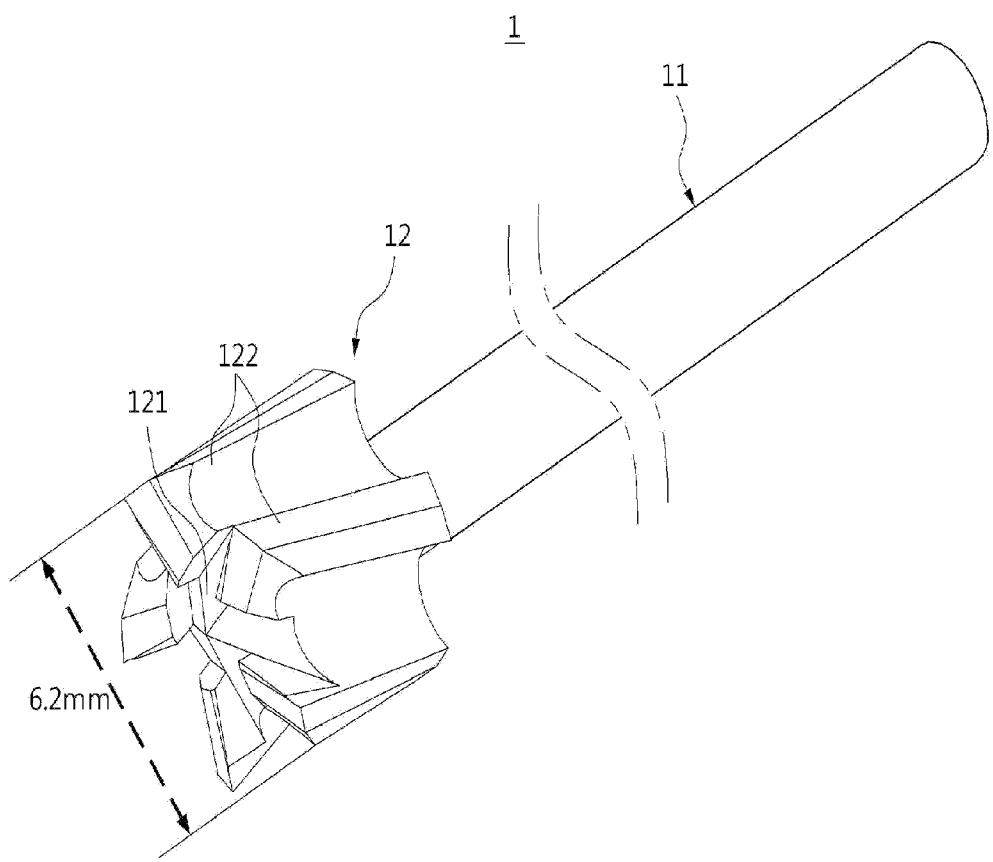
FIG. 8a is a perspective view of an exemplary cutter adapted to a cutting apparatus of a joint cutting system using robot according to an embodiment of the present invention.

Referring to FIG. 8a, the cutting head 12 has multiple cutters 122 protruded equi-angularly at a head core 121, and the outer diameter of the cutting head 12 corresponds to the diameter of the fixing protrusion (a2 in FIG. 2) of the knee joint implant (a in FIG. 2) or is bigger than that by in the range of 10%.

Preferably, the cutting head 12 has 6.2 mm in the outer diameter within a tolerance of 10% and the cutters formed equi-angularly in the head core 121 are five. The diameter of the fixing protrusion (a2) of the implant (a) is generally below 6.0 mm and thickness of the inserted adhesive is to be duly considered in drilling the inserting hole (not shown) in the knee bone where the fixing protrusion is inserted.

As shown in FIG. 8a, if the outer diameter of the cutting head 12 is around 6.2 mm, it is easy to cut the femur, the tibia and so on and, in addition, cut the inserting hole (peg) where the fixing protrusion of the artificial joint implant (a) so that it is needless to change the cutter of 7.8 mm in the diameter and the cutter of 2.3 mm in the diameter during the surgery and the surgery is performed rapidly with one cutter.

Figure 8B:
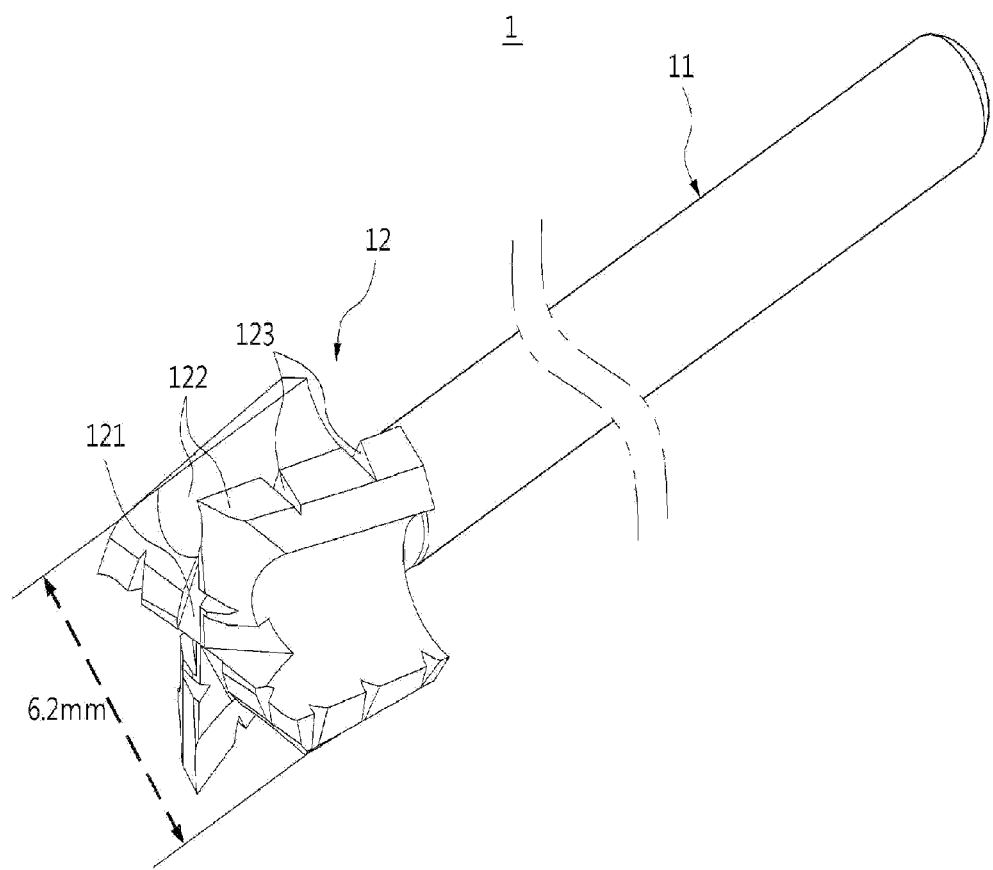
FIG. 8b is a perspective view of another exemplary cutter adapted to a cutting apparatus of a joint cutting system using robot according to an embodiment of the present invention.

FIG. 8b is a perspective view of another exemplary cutter adapted to a cutting apparatus of a joint cutting system using robot according to an embodiment of the present invention.

Referring to FIG. 8b, the outer diameter of the cutting head 12' corresponds, as shown in FIG. 8a, to the diameter of the fixing protrusion (a2 in FIG. 2) of the knee joint implant (a in FIG. 2) or is bigger than that by in the range of 10%. The cutters 122 are 4 and it is characteristic that each cutter 122 has roughing grooves 123. The cutting head 12' has 6.2 mm in the outer diameter within a tolerance of 10%

The roughing groove 123 decreases frictional resistance of the cutter 122 in the rotation of the cutting head 12' and improves the discharge of debris and washing water so that the machinability is improved.

Hereinafter, the function of the cutting apparatus of the joint cutting system using robot according to an embodiment of the present invention will be explained.

First of all, the above mentioned cutter 1 is combined with the cutter support member 2 and the sleeve base 22 is combined with the join part of the robot arm with combining the second base join part 224 with the join part of the robot arm. And then, the shaft 11 of the cuter 1 is combined to be supplied with power by the motor (not shown) in the join part of the robot arm.

After assembling the cutting apparatus, according to the information from a computer the robot arm and the cutter support member 2 moves and then the cutter 1 rotates with cutting the knee bone.

The shaft 11 of the cutter 1 can stably rotate in high speed over 60,00 rpm because it is supported by the first to fourth support bearing 31, 32, 33, 34. Also, the front end of the shaft 11 is supported by the end spacer 5 combined at the front end of the sleeve 212 so that the trembling of the cutting head 12 is decreased.

Meanwhile, when cutting the knee bone (femur, tibia), the cutting head 12 is controlled to move upward and downward or from side to side and therefore the sleeve 21 receives the bending force repeatedly. The bending force is concentrated onto the combining part of the sleeve base 22 and the sleeve 21, the cross sectional area of which is changed rapidly due to the cantilever structure of the sleeve 21, and then great stress to the combining part is forced. However, the reinforcing part 215 in the sleeve 21 restrains the bending force and therefore the transform such like bending is prevented.

Especially, the touch and damage to the bone, the muscle, the skin tissue around surgical site are minimized without the increase of the outer diameter of the sleeve 1 because the support bearings 3 are located at the both ends of the sleeve 21.

In rotating or moving the cutting head 12 upward and downward or from side to side, the shaft 11 is supported by the end spacer 5 combined at the front end of the sleeve body 212, which restrains the bending the cutting head 12.

Owing to the diameter of 6.2 mm the cutting head as shown in FIGS. 8a and 8b can cut easily not only the femur and the tibia, but also the inserting hole (peg) in which the fixing protrusion (a2) of the implant (a) is inserted so that it is needless to change the cutter of 7.8 mm in the diameter with the cutter of 2.3 mm in the diameter, the change such like a existing surgical process, during the surgery and the surgery is performed rapidly and conveniently.

And the cutting head 12 with 5 cutters or the cutting head 12' with roughing groove 123 makes the cutting operation rapid.

Also, the sleeve 21 and the sleeve base 22 are separable so that after overlong using the sleeve 21 alone is changeable not a unit of the sleeve and the sleeve base. Therefore, the advantage is achieved that the maintainability is improved and the maintenance cost is decreased.

Although a few exemplary embodiments have been shown and described, it will be appreciated by those skilled in the art that changes may be made in these exemplary embodiments without departing from the principles and spirit of the invention, the scope of which is defined in the appended claims and their equivalents.

What is claimed is:

1. A cutting apparatus for joint cutting system using robot comprising:
   a shaft combined with a motor in a part of a robot arm;
   a cutter having a cutting head at an end of the shaft;
   a sleeve in which the shaft is inserted;
   a cutter support member having a sleeve base where the sleeve is fixed,
characterized in that the sleeve is a standalone member of a hollow bar with a center hole and is separable from and combinable with the sleeve base,
   wherein the sleeve has support bearings which are equipped in the center hole and support the shaft such that the shaft is rotatable, and in order to reinforce a strength against a bending force, the support bearings are located in a front side and a back side of the sleeve, which minimizes a reduction of a thickness of the sleeve, wherein the sleeve comprises a sleeve body of a hollow bar shape, a join body with a sleeve join part combined with a first base join part at a back end of the sleeve body, bearing install grooves located apart from each other on an inner circular surface of the sleeve for equipping the support bearings, a reinforcing part for reinforcing against a bending force to the sleeve body which is protruded toward a center of the center hole from an inner circular surface of the sleeve body between the bearing install grooves, wherein the support bearings consist of first to fourth support bearings, and wherein each of the first to fourth support bearings has multiple bearings consecutively arranged, an outside surface of which comes into contact with one of the bearing install grooves and an inside surface of which comes into contact with an outer circular surface of the shaft;

reinforcing spacers which are equipped on the inner circular surface of the sleeve between the second support bearing and the fourth support bearing and between the first support bearing and the third support bearing and which has a center hole where the shaft is inserted; and end spacers for retraining a fluctuation of the shaft and having a center hole where the shaft is inserted, one of the end spacers is located between a front end of the center hole of the sleeve and the fourth support bearing and another of the end spacers is located between a back end of the center hole of the sleeve and the third support bearing, wherein a length of the reinforcing part equals to a separation distance between the first support bearing and the second support bearing, and wherein the reinforcing spacers include a first reinforcing spacer of which length equals to a separation distance between the second support bearing and the fourth support bearing.

2. The cutting apparatus of claim 1, wherein the sleeve base comprises a base body with a middle hole part, the first base join part formed on an inner circular surface of the sleeve base around a front end of the sleeve base and combined with a back end of the sleeve, a second base join part formed on the inner circular surface of the sleeve base around a back end of the sleeve base and combined with the part of the robot arm, and a washing water discharging hole formed in the base body for discharging washing water.

3. The cutting apparatus of claim 2, wherein the cutting head has multiple cutters protruded equi-angularly at a head core, and an outer diameter of the cutting head corresponds to a diameter of a fixing protrusion of a knee joint implant or is bigger than the diameter of the fixing protrusion by within 10%.

4. The cutting apparatus of claim 2, wherein the bearing install grooves consist of a first bearing install groove formed on an inner circular surface of the join body with the sleeve join part and a second bearing install groove formed on the inner circular surface of the sleeve body around a front side of the sleeve body, and the first support bearing is combined at a front side of the first bearing install groove, the second support bearing is combined at a back side of the second bearing install groove, the third support bearing is combined at a back side of the first bearing install groove, and the fourth support bearing is combined at the second bearing install groove.

5. The cutting apparatus of claim 4, wherein the cutting head has multiple cutters protruded equi-angularly at a head core, and an outer diameter of the cutting head corresponds to a diameter of a fixing protrusion of a knee joint implant or is bigger than the diameter of the fixing protrusion by within 10%.

6. The cutting apparatus of claim 4, wherein the reinforcing spacers include a second reinforcing spacer of which length equals to a separation distance between the first support bearing and the third support bearing.

7. The cutting apparatus of claim 6, wherein the cutting head has multiple cutters protruded equi-angularly at a head core, and an outer diameter of the cutting head corresponds to a diameter of a fixing protrusion of a knee joint implant or is bigger than the diameter of the fixing protrusion by within 10%.

8. The cutting apparatus of claim 1, wherein the cutting head has multiple cutters protruded equi-angularly at a head core, and an outer diameter of the cutting head corresponds to a diameter of a fixing protrusion of a knee joint implant or is bigger than the diameter of the fixing protrusion by within 10%.

9. The cutting apparatus of claim 8, wherein the number of the cutters is 5 and the outer diameter of the cutting head is 6.2 mm within a tolerance of 10%.

10. The cutting apparatus of claim 8, wherein the cutters have roughing groove for improving machinability, and the outer diameter of the cutting head is 6.2 mm within a tolerance of 10%.

* * * * *